(12) United States Patent
Abe et al.

(10) Patent No.: US 10,717,904 B2
(45) Date of Patent: Jul. 21, 2020

(54) ADHESIVE PREPARATION CONTAINING BISOPROLOL

(71) Applicant: TOA EIYO LTD., Tokyo (JP)

(72) Inventors: Eriko Abe, Osaka (JP); Yu Tachikawa, Osaka (JP); Satoshi Ameyama, Osaka (JP); Naoko Urushihara, Osaka (JP); Jun Ishikura, Osaka (JP); Tetsuya Nakamura, Osaka (JP); Akira Yokouchi, Osaka (JP); Yoshitaka Inoue, Osaka (JP); Kazuhiro Aoyagi, Osaka (JP); Tomoya Tanaka, Osaka (JP); Naohiro Nishida, Fukushima (JP); Kunihiro Minami, Fukushima (JP)

(73) Assignee: TOA EIYO LTD., Chuo-ku, Tokyo (JP)

( * ) Notice: Subject to any disclaimer, the term of this patent is extended or adjusted under 35 U.S.C. 154(b) by 80 days.

(21) Appl. No.: 15/736,516

(22) PCT Filed: Jun. 17, 2016

(86) PCT No.: PCT/JP2016/068036
§ 371 (c)(1),
(2) Date: Dec. 14, 2017

(87) PCT Pub. No.: WO2016/204260
PCT Pub. Date: Dec. 22, 2016

(65) Prior Publication Data
US 2018/0194977 A1    Jul. 12, 2018

(30) Foreign Application Priority Data

Jun. 17, 2015 (JP) ................................ 2015-122405

(51) Int. Cl.
| | | |
|---|---|---|
| *C09J 133/10* | (2006.01) | |
| *A61K 9/70* | (2006.01) | |
| *A61K 31/138* | (2006.01) | |
| *A61K 47/32* | (2006.01) | |
| *A61K 47/14* | (2017.01) | |
| *A61K 47/10* | (2017.01) | |
| *C09J 7/38* | (2018.01) | |
| *C09J 11/06* | (2006.01) | |

(52) U.S. Cl.
CPC .............. *C09J 133/10* (2013.01); *A61K 9/70* (2013.01); *A61K 9/7061* (2013.01); *A61K 31/138* (2013.01); *A61K 47/10* (2013.01); *A61K 47/14* (2013.01); *A61K 47/32* (2013.01); *C09J 7/38* (2018.01); *C09J 11/06* (2013.01)

(58) Field of Classification Search
None
See application file for complete search history.

(56) References Cited

U.S. PATENT DOCUMENTS

| | | |
|---|---|---|
| 2005/0142174 A1 | 6/2005 | Assmus et al. |
| 2007/0140991 A1 | 6/2007 | Maitra et al. |
| 2007/0158227 A1 | 7/2007 | Amano et al. |
| 2011/0104215 A1 | 5/2011 | Ito et al. |
| 2011/0104247 A1* | 5/2011 | Ito .................. A61K 9/7061 424/449 |
| 2011/0124833 A1* | 5/2011 | Ishikura .................. A61L 15/58 526/304 |
| 2012/0265158 A1* | 10/2012 | Braun .................. A61K 9/7061 604/307 |

FOREIGN PATENT DOCUMENTS

| | | |
|---|---|---|
| CN | 102026664 A | 4/2011 |
| CN | 102068699 A | 5/2011 |
| EP | 1 541 177 A1 | 6/2005 |
| EP | 1652508 A1 | 5/2006 |
| EP | 1847264 A1 | 10/2007 |
| JP | 4-150865 A | 5/1992 |
| JP | 2003-313122 A | 11/2003 |
| JP | 2005-519054 A | 6/2005 |
| JP | 2014-105205 A | 6/2014 |
| WO | 2009/119672 A1 | 10/2009 |
| WO | 2011/118683 A1 | 9/2011 |

OTHER PUBLICATIONS

Duro-Tak and Gelva Transdermal Sensitive Adhesives, (Drug Delivery Polymers, 2013) (Year: 2013).*
Communication dated Dec. 17, 2018, issued by the European Patent Office in counterpart European Application No. 16811734.9.
International Search Report issued by the International Searching Authority dated Jul. 26, 2016 in counterpart International Application No. PCT/JP2016/068036 (PCT/ISA/210).
Written Opinion issued by the International Searching Authority dated Jul. 26, 2016 in counterpart International Application No. PCT/JP2016/068036 (PCT/ISA/237).
Communication issued by the Japanese Patent Office dated Jul. 26, 2016 in counterpart Japanese Patent Application No. 2016-120367.
Communication dated Jan. 17, 2020, issued by the Taiwanese Patent Official Action dated Mar. 6, 2020, issued by the Russian Patent Office in counterpart Russian Application No. 2018101449/04.
Substantive Examination Report dated Mar. 9, 2020, issued by the Philippines Intellectual Property Office in corresponding Philippine Application No. 1/2017/502296.
Notification of First Office Action dated Mar. 25, 2020, from the State Intellectual Property Office of People's Republic of China in counterpart Application No. 201680035296.8.
V.M. Sutyagin et al. "Chemistry and physics of polymers" Tomsk Polytechnic University, Publishing house TPU, 2003, (20 pages total).

* cited by examiner Office in counterpart Taiwanese Application No. 105119120.

*Primary Examiner* — Robert A Wax
*Assistant Examiner* — Melissa S Mercier
(74) *Attorney, Agent, or Firm* — Sughrue Mion, PLLC

(57) ABSTRACT

An adhesive preparation containing bisoprolol includes a backing and a pressure-sensitive adhesive layer formed on one side of the backing. The pressure-sensitive adhesive layer contains a polymer prepared through copolymerization of monomer components including a hydroxyl group-containing monomer and an alkyl (meth)acrylate monomer (component (A)), a polymer prepared through copolymerization of monomer components including a methyl methacrylate monomer and a butyl methacrylate monomer (component (B)), and bisoprolol (component (C)).

6 Claims, No Drawings

ADHESIVE PREPARATION CONTAINING BISOPROLOL

TECHNICAL FIELD

One aspect of the present invention relates to an adhesive preparation containing bisoprolol.

BACKGROUND ART

An adhesive preparation to be attached to skin includes a pressure-sensitive adhesive layer formed on one side or both sides of a backing thereof and is intended to administer a drug from the skin to the body via the pressure-sensitive adhesive layer to prevent or treat a disease locally or in a whole body.

Such an adhesive preparation is required to have sufficient adhesiveness on attaching to a skin, and is required to be able to be peeled and removed from the skin without causing contamination of the surface of skin after use (for example, occurrence of adhesive deposit, stickiness or the like). In addition, the adhesive preparation is desirably low in irritation to the skin.

PTL 1 discloses an adhesive preparation that uses an acrylic pressure-sensitive adhesive obtained through polymerization of an alkyl (meth)acrylate and a monomer copolymerizable with the alkyl (meth)acrylate and containing neither a carboxyl group nor a sulfo group. Further, in the adhesive preparation in the literature, the pressure-sensitive adhesive layer contains an organic liquid component and is crosslinkable. The adhesive preparation is said to have a sufficient cohesive power so as not to cause adhesive deposit in peeling, be low in irritation to the skin and have a soft feeling. However, the pressure-sensitive adhesive having neither a carboxyl group nor a sulfo group disclosed in PTL 1 possibly peels off from the skin when it is attached to a skin surface for a long period of time or when it is attached to a largely moving skin surface, and further improvement of adhesive properties is required.

PTL 2 discloses an adhesive preparation that contains, in the pressure-sensitive adhesive layer thereof, a crosslinked product of a copolymer formed of an alkyl (meth)acrylate or a mixture of the ester and an alkoxyalkyl (meth)acrylate, and a monomer containing a carboxyl group and/or a hydroxyl group. However, when the pressure-sensitive adhesive layer in the adhesive preparation contains a carboxyl group-containing copolymer and bisoprolol as a drug, there is a concern that the carboxyl group is subjected to the action of bisoprolol to disturb release of the drug from the adhesive preparation, thereby lowering the utilization rate of the drug.

On the other hand, when a hydroxyl group-containing copolymer is contained, good adhesiveness to skin is exhibited and there would be no concern that the release of the bisoprolol from the adhesive preparation is disturbed. However, the hydroxyl group may be subjected to the action of bisoprolol to cause deviation of pressure-sensitive adhesive properties, for example, increase in holding power thereof during preservation, etc.

CITATION LIST

Patent Literature

PTL 1: JP-A-2003-313122
PTL 2: JP-A-H04-150865

SUMMARY OF INVENTION

Technical Problem

The present invention has been found in consideration of the above-mentioned situation, and in one aspect of the present invention, the technical problem is to provide a bisoprolol-containing adhesive preparation capable of maintaining good pressure-sensitive adhesive properties and having high dermal permeability of bisoprolol.

Solution to Problem

The present inventors have made assiduous studies for the purpose of solving the above-mentioned problems, and as a result, they have found that, when a bisoprolol-containing pressure-sensitive adhesive layer contains a polymer prepared through copolymerization of monomer components including a hydroxyl group-containing monomer and an alkyl (meth)acrylate monomer, and a polymer prepared through copolymerization of monomer components including a methyl methacrylate monomer and a butyl methacrylate monomer, the good pressure-sensitive adhesive properties can be maintained (especially good pressure-sensitive adhesive properties can be maintained even when a large amount of an organic liquid component is contained), and the present invention has been completed.

That is, one aspect of the present invention is as follows.

[1] An adhesive preparation containing bisoprolol, comprising a backing and a pressure-sensitive adhesive layer formed on one side of the backing, wherein the pressure-sensitive adhesive layer contains the following component (A) to component (C):

component (A): a polymer prepared through copolymerization of monomer components including a hydroxyl group-containing monomer and an alkyl (meth)acrylate monomer;

component (B): a polymer prepared through copolymerization of monomer components including a methyl methacrylate monomer and a butyl methacrylate monomer; and component (C): bisoprolol.

[2] The adhesive preparation containing bisoprolol according to [1], wherein the pressure-sensitive adhesive layer further contain an organic liquid component.

[3] The adhesive preparation containing bisoprolol according to [1] or [2], wherein a content ratio of the component (A) to the component (B) (component (A)/component (B)) is 1/0.05 to 1/1 by weight.

Advantageous Effects of Invention

The bisoprolol-containing adhesive preparation in one aspect of the present invention can maintain good pressure-sensitive adhesive properties (especially can maintain good pressure-sensitive adhesive properties even when a large amount of an organic liquid component is contained), and can have high dermal permeability of bisoprolol.

DESCRIPTION OF EMBODIMENTS

One aspect of the present invention is described in more detail hereinunder with reference to preferred embodiments thereof.

The bisoprolol-containing adhesive preparation in one aspect of the present invention is provided as a transdermal preparation, specifically, as a matrix-type adhesive preparation, a reservoir-type adhesive preparation, etc.

The backing in the bisoprolol-containing adhesive preparation in one aspect of the present invention (hereinafter also referred to as "adhesive preparation" in one aspect of the present invention) is not specifically limited, and any backing may be used as long as the pressure-sensitive adhesive layer can be formed and hold on one surface thereof. Specific examples thereof include single-layered materials or laminated materials of various plastic films such as polyesters (for example, polyethylene terephthalate, etc.), polyamides (for example, nylon, etc.), polyethylene, polypropylene, polyvinyl chloride, polyvinylidene chloride (trade name, SARAN, etc.), ionomer resins (trade name: SYRLYN, etc.), polytetrafluoroethylene, ethylene-acrylate copolymers, ethylene-vinyl alcohol copolymers (trade name: EVAL, etc.) and the like, various metal foils and the like. For enhancing the anchoring force with the pressure-sensitive adhesive layer to be formed on the backing, the surface of the backing may be processed for forming an undercoat layer thereon, or for corona discharge treatment, plasma irradiation treatment, primer treatment or the like, and further, a backing on which a porous sheet is laminated on the side of the adhesive layer-forming surface of the backing is preferably used. Practically, examples of the porous sheet in this case include paper, nonwoven fabrics, woven fabrics, knitted fabrics, perforated plastic sheets, etc. Among these, from the viewpoint of feeling in use during adhesion and adhesion operability, it is preferred to use paper, nonwoven fabrics or woven fabrics.

The thickness of the backing in the bisoprolol-containing adhesive preparation is preferably 10 to 200 μm from the viewpoint of improvement of anchoring, and flexibility and adhesion operability of the entire transdermal preparation, and in the case of a thin adhesive preparation, a backing having a thickness in a range of 10 to 100 μm is employable. When a nonwoven fabric or a woven fabric is used as the porous sheet, the basis weight thereof may be 5 to 30 $g/m^2$, preferably 6 to 15 $g/m^2$. The most preferred backing in one aspect of the present invention is a laminated film of a polyester film having a thickness of 1.5 to 6 μm and a nonwoven polyester fabric having a basis weight of 6 to 12 $g/m^2$, or an ethylene-vinyl alcohol copolymer film having a thickness of 10 μm to 80 μm.

When an undercoat layer is formed on the surface of the backing, the undercoat layer preferably contains porous inorganic particles. Further, the undercoat layer preferably contains a binder resin for adhering the porous inorganic particles to the backing.

Examples of the porous inorganic particles include porous silica particles, porous alumina particles, porous titania particles, etc. Among them, porous silica particles are preferably used since the particles are hardly broken in a production process or in a dispersion liquid. One kind alone or two or more kinds of porous inorganic particles may be used either singly or as combined.

Any adequate resin is employable as the binder resin so far as it is used for adhering porous inorganic particles to the backing. For example, examples thereof include an urethane resin, an ethyleneimine resin, an aminoethyl resin, a polyester resin, a polyolefin resin, an ethylene-vinyl alcohol copolymer resin, etc.

The porous inorganic particles and the binder resin are dispersed or dissolved in an adequate solvent to prepare a solution for an undercoat layer. As the solvent, those having excellent dispersibility of porous inorganic particles and having excellent miscibility with the binder resin may be adequately selected. Specific examples of the solvent include water, methanol, ethanol, 1-propanol, 2-propanol, ethyl acetate, methyl ethyl ketone, toluene, etc. One kind alone or two or more kinds thereof may be used either singly or as combined. The solid concentration in the undercoat layer solution may be set to be any suitable value in consideration of handleability, etc.

By applying the undercoating solution onto the surface of the backing and drying and/or curing it thereon, an undercoat layer may be formed.

The basis weight of the undercoat layer may be suitably set depending on the kind, use or purpose of the backing or the pressure-sensitive adhesive layer. The basis weight is preferably 0.1 to 10 $g/m^2$, more preferably 0.1 to 8 $g/m^2$, even more preferably 0.2 to 5 $g/m^2$. Having such a basis weight, a uniform undercoat layer can be formed and a good anchoring can be given.

For protecting the pressure-sensitive adhesive surface of the pressure-sensitive adhesive layer in the adhesive preparation in one aspect of the present invention until use, a release liner is preferably laminated to the pressure-sensitive adhesive surface. The release liner is not specifically limited so far as it can ensure sufficiently light peelability. Specific examples thereof include plastic films such as polyesters, polyvinyl chloride, polyvinylidene chloride, polyethylene terephthalate or the like, paper such as high-quality paper, glassine paper or the like, as well as laminate films (the side where the pressure-sensitive adhesive layer is contacted is paper) of paper such as high-quality paper, glassine paper or the like with polyolefin, for which releasing treatment has been made by applying a silicone resin, a fluororesin or the like onto the surface thereof. The thickness of the release liner is generally 10 to 200 μm, preferably 25 to 100 μm.

The polymer prepared through copolymerization of monomer components including a hydroxyl group-containing monomer and an alkyl (meth)acrylate monomer, which is the component (A) contained in the pressure-sensitive adhesive layer, is not specifically limited so far as the monomers are copolymerized in such a manner that the proportion of the alkyl (meth)acrylate unit could be 40% by weight or more, preferably 40 to 99% by weight, more preferably 40 to 90% by weight, even more preferably 50 to 90% by weight, per the entire polymer of the component (A), and that the polymer could contain a hydroxyl group in the molecule thereof.

In this description, "(meth)acryl" means both "acryl" and "methacryl".

Not specifically limited thereto, the alkyl (meth)acrylate monomer is preferably an alkyl (meth)acrylate monomer having an alkyl group having 4 or more carbon atoms from the viewpoint of adhesiveness, and specific examples thereof include an alkyl (meth)acrylate monomer in which the alkyl group is a linear alkyl group or branched alkyl group having 4 to 13 carbon atoms such as an n-butyl group, an isobutyl group, a sec-butyl group, a tert-butyl group, an n-pentyl group, an isopentyl group, a neopentyl group, a hexyl group, a heptyl group, an octyl group, a 2-ethylhexyl group, a nonyl group, a decyl group, an undecyl group, a dodecyl group, a tridecyl group, etc. Among them, 2-ethylhexyl acrylate is preferred. One kind or two or more kinds of alkyl (meth)acrylate monomers may be used.

The hydroxyl group-containing monomer is not specifically limited, and any hydroxyl group-containing monomer having at least one unsaturated double bond participating in copolymerization reaction in the molecule can be used. Examples thereof include N-hydroxyalkyl(meth)acrylamides, hydroxyethyl (meth)acrylate, hydroxypropyl (meth)acrylate, etc., and preferable examples thereof include N-hydroxyalkylacrylamides, hydroxyethyl acrylate and hydroxypropyl acrylate. Here, N-hydroxyalkyl(meth)acrylamides are preferably N-hydroxyalkyl($C_{1-4}$)(meth)acrylamides in which the alkyl group has 1 to 4 carbon atoms, more preferably N-hydroxyalkyl($C_{2-4}$)acrylamides in which the alkyl group has 2 to 4 carbon atoms. The alkyl group in the hydroxyalkyl group may be linear or branched. As the N-hydroxyalkyl(meth)acrylamides, examples thereof include N-(2-hydroxyethyl)acrylamide, N-(2-hydroxyethyl)methacrylamide, N-(2-hydroxypropyl)acrylamide, N-(2-hydroxypropyl)methacrylamide, N-1-hydroxypropyl)acrylamide, N-(1-hydroxypropyl)methacrylamide, N-(3-hydroxypropyl)acrylamide, N-(3-hydroxypropyl)methacrylamide, N-(2-hydroxybutyl)acrylamide, N-(2-hydroxybutyl)methacrylamide, N-(3-hydroxybutyl)acrylamide, N-(3-hydroxybutyl)methacrylamide, N-(4-hydroxybutyl)acrylamide, N-(4-hydroxybutyl)methacrylamide, etc.

As the hydroxyl group-containing monomer, preferable examples thereof include N-(2-hydroxyethyl)acrylamide and N-(2-hydroxyethyl)methacrylamide, and N-(2-hydroxyethylacryl)amide is most preferred.

One kind or two or more kinds of hydroxyl group-containing monomers may be used.

The hydroxyl group-containing monomer is contained in a range of preferably 1 to 20% by weight, more preferably 1 to 15% by weight, even more preferably 5 to 10% by weight, per the entire polymer of the component (A). When the content is lower than the lower limit, the compatibility with additives such as an organic liquid component or the like may be poor, so that such additives are possibly unable to be held, and when the content is more than the upper limit, the polymer would be readily subjected to the action of bisoprolol to cause significant fluctuation of physical properties with time.

The polymer as the component (A) may be a polymer further copolymerized with any monomer(s) other than the alkyl (meth)acrylate monomer and the hydroxyl group-containing monomer (hereinafter this may also be referred to as "third monomer"). When the third monomer is contained as the monomer component to constitute the polymer as the component (A), the content thereof is preferably 50% by weight or less, more preferably 1 to 50% by weight, even more preferably 5 to 45% by weight, especially preferably 10 to 45% by weight, and most preferably 20 to 45% by weight, in the polymer as the component (A). Copolymerization with the third monomer makes it possible to control the pressure-sensitive adhesiveness and the cohesive power of the adhesive preparation, and makes it possible to control the solubility and the releasability of a drug. When the content of the third monomer in the polymer is more than 50% by weight, the tackiness or pressure-sensitive adhesiveness of the adhesive preparation obtained may lower.

As the third monomer, a monomer containing nitrogen (N) as the constituent atom (but excluding a monomer containing nitrogen (N) as the constituent atom of the above-mentioned hydroxyl group-containing monomer) is usable. Examples of the nitrogen atom-containing monomer include N-vinyl-cyclic amides such as N-vinyl-2-pyrrolidone, N-vinyl-2-piperidone, N-vinyl-3-morpholinone, N-vinyl-2-caprolactam, N-vinyl-1,3-oxazin-2-one, N-vinyl-3,5-morpholinedione, etc. Among them, N-vinyl-2-pyrrolidone is most preferred.

Preferably, the polymer as the component (A) has a weight-average molecular weight (Mw) falling within a range of 1,400,000 to 2,400,000, more preferably 1,600,000 to 2,200,000. Having a weight-average molecular weight (Mw) falling within the preferred range, the polymer can have an increased power to retain an organic liquid component in the pressure-sensitive adhesive layer and can ensure an increased cohesive power of the pressure-sensitive adhesive layer, and thus, good pressure-sensitive adhesive properties can be exhibited.

In one aspect of the present invention, the weight-average molecular weight (Mw) is measured in accordance with a multiangle light scattering (MALS) method. Specifically, the weight-average molecular weight may be determined by MALS, as follows. As a measuring device, DAWN DSP manufactured by Wyatt Technology is used as a detector, a polymer dissolved in tetrahydrofuran and ethanol is continuously injected into the device with a syringe pump, and using a calibration curve of standard polyethylene, the weight-average molecular weight is calculated.

The component (B) contained in the pressure-sensitive adhesive layer is a polymer prepared through copolymerization of monomer components including a methyl methacrylate monomer and a butyl methacrylate monomer. The content ratio of the methyl methacrylate monomer to the butyl methacrylate monomer in the polymer is preferably 1/1 to 1/4 by weight, more preferably 1/3 by weight. The side chain of the polymer is a neutral group. Consequently, as compared with a polymer containing a basic group or an acidic group in the side chain, good stability of containing bisoprolol in the pressure-sensitive adhesive layer with time can be obtained.

The weight-average molecular weight (Mw) of the polymer of the component (B) is preferably within a range of 100,000 to 200,000, more preferably 130,000 to 170,000. Having a weight-average molecular weight (Mw) falling within the preferred range, the compatibility with the component (A) is good and good pressure-sensitive adhesive properties can be obtained.

The content ratio of the component (A) to the component (B) contained in the pressure-sensitive adhesive layer (component (A)/component (B)) is preferably 1/0.05 to 1/1 by weight, more preferably 1/0.05 to 1/0.8 by weight. When the content ratio of the component (B) to the component (A) (component (B)/component (A)) is less than 0.05, good pressure-sensitive adhesive properties could not be obtained, and when the content ratio (component (B)/component (A)) is more than 1, the component (A) and the component (B) would mix ununiformly when producing the adhesive preparation, or the phase separation tends to be occurred with time.

"Bisoprolol" as the component (C) contained in the pressure-sensitive adhesive layer includes not only the free form of bisoprolol but also a hydrochloride or an organic acid salt thereof. If desired, two or more kinds of salts of bisoprolol may be used as combined. The content of bisoprolol in the pressure-sensitive adhesive layer may fall within a range capable of satisfying the drug effect of bisoprolol and not detracting from the adhesiveness of the pressure-sensitive adhesives. From the viewpoint of the interaction with the polymer containing a hydroxyl group-containing monomer and a (meth)acrylate and of the effect of the drug, bisoprolol is contained preferably in an amount of 0.1 to 40% by weight, more preferably 1 to 30% by weight, based on the total weight of the pressure-sensitive adhesive layer.

The pressure-sensitive adhesive layer may contain any component having an effect for improving an adhesive feeling with no specific limitation, and for example, an organic liquid component may be contained. Examples of the organic liquid component include glycols such as ethylene glycol, diethylene glycol, propylene glycol, triethylene glycol, polyethylene glycol, polypropylene glycol, etc.; oils and fats such as olive oil, castor oil, squalane, lanolin, etc.; hydrocarbons such as liquid paraffin, etc.; various surfactants; ethoxylated stearyl alcohol; glycerin esters (monoglycerides, diglycerides, triglycerides or mixtures thereof) of long-chain or middle-chain fatty acids such as oleic acid, caprylic acid, lauric acid, etc.; monoalcohol fatty acid esters (preferably monoalcohol fatty acid esters of fatty acid having 6 to 22 carbon atoms, more preferably 12 to 16 carbon atoms and alcohols having 1 to 20 carbon atoms) such as ethyl laurate, isopropyl myristate, isotridecyl myristate, octyl palmitate, isopropyl palmitate, ethyl oleate, diisopropyl adipate, etc.; higher fatty acids (preferably higher fatty acids having 8 to 22 carbon atoms) such as oleic acid, caprylic acid, etc.; higher alcohols (preferably higher alcohols having 6 to 22 carbon atoms) such as oleyl alcohol, etc.; polyalcohol fatty acid esters such as propylene glycol monolaurate, propylene glycol monooleate, propylene glycol monostearate, etc.; citrates such as triethyl citrate, triethyl acetylcitrate, tributyl citrate, tributyl acetylcitrate, etc.; N-methylpyrrolidone; 1,3-butanediol, etc. Among them, higher alcohols, monoalcohol fatty acid esters, glycerin esters (preferably monoglycerides) of long-chain or middle-chain fatty acids, and citrates are preferred; and higher alcohols, monoalcohol fatty acids are more preferred; and isopropyl myristate, diisopropyl adipate and oleyl alcohol are most preferred.

The content of the organic liquid component in the pressure-sensitive adhesive layer is preferably 0.1 to 2.5 parts by weight, more preferably 0.2 to 2.0 parts by weight, even more preferably 0.3 to 1.5 parts by weight, relative to 1 part by weight of the total content of the component (A) and the component (B). When the content of the organic liquid components satisfies the above-mentioned range, further better adhesiveness to skin and low skin-irritating properties can be obtained, and adhesive feeling can be improved.

The pressure-sensitive adhesive layer may further contain not only the above-mentioned liquid component but also any other component within a range not detracting from the advantageous effects of the present invention. Examples of the optional component include antioxidants such as ascorbic acid, tocopherol acetate, natural vitamin E, dibutylhydroxytoluene, butylhydroxyanisole, etc.; amine-ketone antiaging agents such as 2,6-tert-butyl-4-methylphenol, etc.; aromatic secondary amine antiaging agents such as N,N'-di-2-naphthyl-p-phenylenediamine, etc.; monophenolic antiaging agents such as 2,2,4-trimethyl-1,2-dihydroquinoline polymer, etc.; bisphenolic antiaging agents such as 2,2'-methylenebis(4-ethyl-6-tert-butylphenol), etc.; polyphenolic antiaging agents such as 2,5-tert-butylhydroquinone, etc.; fillers such as kaolin, hydrous silicon dioxide, zinc oxide, starch acrylate 1000, etc.; softeners such as polybutene, macrogol 1500, etc.; preservatives such as benzoic acid, sodium benzoate, chlorohexidine hydrochloride, sorbic acid, methyl paraoxybenzoate, butyl paraoxybenzoate, etc.; colorants such as yellow iron oxide, yellow iron sesquioxide, iron sesquioxide, black iron oxide, carbon black, carmine, β-carotene, copper chlorophyll, food blue No. 1, food yellow No. 4, food red No. 2, licorice extract, etc.; refreshing agents such as fennel oil, d-camphor, dl-camphor, peppermint oil, d-borneol, l-menthol, etc.; fragrances such as spearmint oil, clove oil, vanillin, bergamot oil, lavender oil, etc.

The thickness of the pressure-sensitive adhesive layer in one aspect of the present invention is not specifically limited. For example, the thickness of the pressure-sensitive adhesive layer is preferably 5 to 400 µm, more preferably 7 to 200 µm, even more preferably 10 to 100 µm. Having the above-mentioned thickness, good pressure-sensitive adhesive properties (for example, adhesion strength) can be realized.

The pressure-sensitive adhesive layer may be formed by applying a coating liquid for forming the pressure-sensitive adhesive layer onto a backing or a release liner (typically by coating with the liquid), and drying it to remove the solvent. The coating liquid for forming the pressure-sensitive adhesive layer contains the pressure-sensitive adhesive layer in one aspect of the present invention and a suitable solvent capable of dissolving the composition.

EXAMPLES

Hereinunder, one aspect of the present invention is described more specifically by showing examples thereof. The present invention should not be restricted by the description of examples.
[Preparation of Component (A)]
Preparation of Polymer (A1)

In a reactor equipped with a cooling tube, a nitrogen gas-introducing tube, a thermometer, a dropping funnel and a stirrer, 70 parts by weight of 2-ethylhexyl acrylate (hereinafter may be expressed as "2-EHA"), 5 parts by weight of N-(2-hydroxyethyl)acrylamide (hereinafter may be expressed as "HEAA"), 25 parts by weight of N-vinyl-2-pyrrolidone (hereinafter may be expressed as "N-VP"), and 333.3 parts by weight of ethyl acetate as a solvent were put, and they were stirred for 1 hour while bubbling a nitrogen gas (100 mL/min) at room temperature. Subsequently, the contents in the reactor were heated, and when they reached 60° C., 0.2 parts of 2,2'-azobisisobutyronitrile (AIBN) as a polymerization initiator was added thereto. Under control of the temperature of the contents at 60° C., the polymerization was performed for 6 hours in a nitrogen gas stream atmosphere, followed by keeping it at 76° C. for 15 hours. By the solution polymerization in the manner as described above, a pressure-sensitive adhesive composition which was a solution of an acrylic copolymer (2-EHA/HEAA/N-VP=70/5/25 (by weight), Mw: 2,200,000) (substantially, a coating liquid for forming a pressure-sensitive adhesive layer, the same shall apply to Examples 2 to 3 and Comparative Examples 1 to 3) was obtained.
Preparation of Polymer (A2)

This was prepared in the same manner as that for the polymer (A1) except that 2-EHA was 55 parts by weight, HEAA was 5 parts by weight and N-VP was 40 parts by weight. Mw was 2,000,000.

The polymer (A1) or the polymer (A2) was used as the component (A).

As the component (B), a copolymer of a methyl methacrylate monomer and a butyl methacrylate monomer in a content ratio of 1:3 by weight (Plastoid B (trade name) manufactured by Rohm Pharma, weight-average molecular weight 150,000) (Polymer (B1)) was used.

As an organic liquid component, isopropyl myristate (IPM), diisopropyl adipate (DIPA) or oleyl alcohol (OA) was used.

As the component (C), bisoprolol was used in a free form.

Example 1

55 parts by weight (as a solid content) of the polymer (A1) as the component (A), 10 parts by weight of the polymer (B1) as the component (B), 5 parts by weight of bisoprolol in a free form as the component (C), and 30 parts by weight of isopropyl myristate as an organic liquid component were mixed, and stirred along with an adequate amount of ethyl acetate added thereto for concentration control, thereby preparing a uniform pressure-sensitive adhesive solution. The resultant pressure-sensitive adhesive solution was applied onto the release-treated surface of a polyester release sheet having a thickness of 75 μm, in such a manner that the dry thickness thereof could be 45 μm, followed by drying at 80° C. for 5 minutes to form a pressure-sensitive adhesive layer. Next, a laminate of a polyester film having a thickness of 4 μm and a polyester nonwoven fabric having a basis weight of 12 g/m² was used as a backing, and the nonwoven fabric surface of the laminate was limited to the pressure-sensitive adhesive layer under pressure, thereby producing a bisoprolol-containing adhesive preparation in one aspect of the present invention.

Examples 2 and 3, and Comparative Example 1

The bisoprolol-containing adhesive preparations of Examples 2 and 3 and Comparative Example 1 each having the composition shown in Table 1 were produced in the same process as in Example 1.

Example 4

52 parts by weight (as a solid content) of the polymer (A2) as the component (A), 5 parts by weight of the polymer (B1) as the component (B), 13 parts by weight of bisoprolol as the component (C), and 30 parts by weight of isopropyl myristate as an organic liquid component were mixed, and stirred along with an adequate amount of ethyl acetate added thereto for concentration control, thereby preparing a uniform pressure-sensitive adhesive solution. The resultant pressure-sensitive adhesive solution was applied onto the release-treated surface of a polyester release sheet having a thickness of 75 μm, in such a manner that the dry thickness thereof could be 17 μm, followed by drying at 80° C. for 5 minutes to form a pressure-sensitive adhesive layer. On the other hand, an ethylene-vinyl alcohol copolymer resin and porous silica particles (Sylysia 350 manufactured by Fuji Silysia Chemical) were dissolved and dispersed in a blending ratio (by weight) of 1:1, in a mixed solvent of n-propanol and water (n-propanol/water=7/3, by volume) to prepare an undercoating agent. The resultant undercoating agent was applied onto one side of an ethylene-vinyl alcohol copolymer film having a thickness of 15 μm, as a backing, in such a manner that the basis weight of the coating film (undercoat layer) after dried could be 0.7 g/m2, followed by drying to form an undercoat layer, thereby preparing a backing.

The pressure-sensitive adhesive layer was laminated under pressure to the undercoated surface of the backing to produce a bisoprolol-containing adhesive preparation in one aspect of the present invention.

Examples 5 to 13, Comparative Examples 2 to 5

The bisoprolol-containing adhesive preparations of Examples 5 to 13 and Comparative Examples 2 to 5 each having the composition shown in Table 1 were produced in the same process as in Example 4.

TABLE 1

| | \[Part by weight\] | | | | | | |
|---|---|---|---|---|---|---|---|
| | Component (A) | | Component (B) | Component (C) | Liquid Component | | |
| | A1 | A2 | B1 | | IPM | DIPA | OA |
| Example 1 | 55 | — | 10 | 5 | 30 | — | — |
| Example 2 | 55 | — | 12 | 5 | 28 | — | — |
| Example 3 | 55 | — | 15 | 5 | 25 | — | — |
| Example 4 | — | 52 | 5 | 13 | 30 | — | — |
| Example 5 | — | 47 | 10 | 13 | 30 | — | — |
| Example 6 | — | 47 | 10 | 13 | — | 30 | — |
| Example 7 | — | 44 | 13 | 13 | 30 | — | — |
| Example 8 | — | 44 | 18 | 13 | 25 | — | — |
| Example 9 | — | 42 | 21 | 13 | 24 | — | — |
| Example 10 | — | 42 | 21 | 13 | — | — | 24 |
| Example 11 | — | 39 | 23 | 13 | 25 | — | — |
| Example 12 | — | 37 | 26 | 13 | 24 | — | — |
| Example 13 | — | 35 | 28 | 13 | 24 | — | — |
| Comparative Example 1 | 65 | — | — | 5 | 30 | — | — |
| Comparative Example 2 | — | 52 | — | 13 | 35 | — | — |
| Comparative Example 3 | — | 47 | — | 13 | 40 | — | — |
| Comparative Example 4 | — | 44 | — | 13 | 43 | — | — |
| Comparative Example 5 | — | 42 | — | 13 | 45 | — | — |

1. <Cohesive Property> (Organoleptic Evaluation)

The release liner was peeled from the adhesive preparation, and the exposed surface of the pressure-sensitive adhesive layer was touched with fingers to visually evaluate the cohesive property of the pressure-sensitive adhesive layer in accordance with the following indices.

A: No stringiness, and no adhesive deposit left on fingers.
B: Much stringiness, and adhesive deposit left on fingers.

2. <Adhesive Force>

Each adhesive preparation was cut into a size of 12 mm or more in width×40 mm or more in length to use as a test piece. The release liner was removed from the test piece, and in accordance with JIS Z0237:2009, the test piece was adhered to a test plate (Bakelite plate) under pressure by a 2-kg rubber roller to run thereon for one lap, and then left in an atmosphere of 23° C. for 30 minutes. Subsequently, this was fixed to a tensile tester, and the lead of the test piece was folded by 180 degrees and peeled by pulling at a speed of 300 mm/min. The load at three points at nearly the same intervals was read, and the mean value of the data was referred to as an adhesive force (N/12 mm width). After the test, the Bakelite plate was visually checked for the presence or absence of adhesive deposit thereon, from which the cohesive property of the test piece was evaluated.

3. <Holding Power>

Each adhesive preparation was cut into a size of 10 mm in width×50 mm in length to use as a test piece. The release liner was removed from the test piece, and in accordance with JIS Z0237:2009, the test piece was adhered to one end (10 mm in width and 20 mm in length) of a test plate (Bakelite plate) under pressure by a 2-kg rubber roller to run thereon for one lap, and the other end was reinforced with reinforcing paper. This was fixed to a hook in an apparatus stabilized at a temperature of 40±5° C., and left as such for 30 minutes. Subsequently, a load of 100 g was applied thereto, and the time taken before dropping down was referred to as a holding power (minute). The number of tests was n=3, and the data in the three tests were averaged.

4. <Skin Permeation Test>

The adhesive preparations obtained in Examples 5 and 9 and Comparative Examples 3 and 5 were individually cut into a nearly circular form having a diameter of 8 mm. The release liner was removed, and the test piece was attached to the cuticle face of the excised skin of a hairless mouse as blanked in a nearly circular form having a diameter of 20 mm.

The hairless mouse exposed skin was set in a skin permeation test cell (application area: 6 mmφ) in such a manner that the cuticle layer side could be a donor phase and the dermis side could be a receptor phase, and in the receptor phase, physiological saline was put. Under the condition, the skin permeation test was carried out at 32° C. for 12 hours. The receptor liquid after 24 hours was collected, and the drug concentration therein was measured through high-performance liquid chromatography (HPLC). The number of tests was n=3, and the data in the three tests were averaged.

<HPLC Condition>

Column: YMC-Pack C8 (particle diameter 5 μm, inner diameter 4.6 mm×length 150 mm) manufactured by YMC, mobile phase: pH 2.5 phosphoric acid buffer/acetonitrile=7/3

Detection Wavelength: 225 nm
Flow Rate: 0.75 mL/min
Column Temperature: 40° C.

As shown in Table 2, the bisoprolol-containing adhesive preparations of Examples 1 to 3 in one aspect of the present invention were given a rank A for the cohesive property. As opposed to these, the cohesive property in Comparative Example 1 was given a rank B, that is, it was evaluated to give more adhesive deposit to fingers, as compared with the cases of Examples 1 to 3.

As shown in Table 2, the bisoprolol-containing adhesive preparations of Examples 4 to 13 in one aspect of the present invention were given a rank A for the cohesive property, from which it was found that these samples had good pressure-sensitive adhesive properties in point of both the adhesive force and the holding power. In addition, the cases of Examples 5 and 9 also provided good results in the skin permeation test.

As opposed to these, the cohesive property in Comparative Examples 2 to 5 was given a rank B, that is, it was found that the cohesive failure occurred in the comparative samples and the comparative samples were evaluated to give more adhesive deposit to fingers, as compared with the cases of Examples. The cases of Comparative Examples 3 and 5 provided good results in the skin permeation test, but regarding the pressure-sensitive adhesive properties, the cohesive failure occurred in these comparative samples and the comparative samples are not suitable for practical use as adhesive preparations.

TABLE 2

|  | Cohesive Property | Adhesive Force (N/12 mm width) | Holding Power (min) | Skin Permeation Test (μg/cm² · 12 h) |
| --- | --- | --- | --- | --- |
| Example 1 | A | — | — | — |
| Example 2 | A | — | — | — |
| Example 3 | A | — | — | — |
| Example 4 | A | 1.1 | 92.1 | — |
| Example 5 | A | 1.1 | 41.4 | 175.3 |
| Example 6 | A | 1.3 | 81.6 | — |
| Example 7 | A | 1.2 | 24.7 | — |
| Example 8 | A | 1.2 | 73.4 | — |
| Example 9 | A | 1.2 | 77.8 | 179.9 |
| Example 10 | A | 1.4 | 40 | — |
| Example 11 | A | 1.3 | 59.3 | — |
| Example 12 | A | 1.6 | 71.2 | — |
| Example 13 | A | 1.6 | 80.6 | — |
| Comparative Example 1 | B | — | — | — |
| Comparative Example 2 | B | — | — | — |
| Comparative Example 3 | B | 2.7* | 9.1 | 182.6 |
| Comparative Example 4 | B | 2.6* | 9.1 | — |
| Comparative Example 5 | B | 2.3* | 6.7 | 207.2 |

*Cohesive failure occurred.
In the Table, "—" means unmeasured.

While the present invention has been described in detail and with reference to specific embodiments thereof, it will be apparent to one skilled in the art that various changes and modifications can be made therein without departing from the spirit and scope thereof.

The present application is based on Japanese patent application No. 2015-122405 filed on Jun. 17, 2015, the contents of which are incorporated herein by reference.

INDUSTRIAL APPLICABILITY

In the bisoprolol-containing adhesive preparation in one aspect of the present invention, good pressure-sensitive adhesive properties can be maintained (especially good pressure-sensitive adhesive properties can be maintained even when a large amount of an organic liquid component is contained), and the adhesive preparation can have high dermal permeability of bisoprolol.

The invention claimed is:

1. An adhesive preparation containing bisoprolol, comprising a backing and a pressure-sensitive adhesive layer formed on one side of the backing, wherein the pressure-sensitive adhesive layer contains the following component (A) to component (C):
   component (A): a polymer prepared through copolymerization of monomer components including a hydroxyl group-containing monomer, an alkyl (meth)acrylate monomer, and N-vinyl-cyclic amide monomer;
   component (B): a polymer prepared through copolymerization of monomer components including a methyl methacrylate monomer and a butyl methacrylate monomer; and
   component (C): bisoprolol.

2. The adhesive preparation containing bisoprolol according to claim 1, wherein the pressure-sensitive adhesive layer further contains an organic liquid component.

3. The adhesive preparation containing bisoprolol according to claim 1, wherein a content ratio of the component (A) to the component (B) (component (A)/component (B)) is 1/0.05 to 1/1 by weight.

4. The adhesive preparation containing bisoprolol according to claim 2, wherein a content ratio of the component (A) to the component (B) (component (A)/component (B)) is 1/0.05 to 1/1 by weight.

5. The adhesive preparation containing bisoprolol according to claim 1, wherein the hydroxyl group-containing monomer includes N-hydroxyalkyl(meth)acrylamide.

6. The adhesive preparation containing bisoprolol according to claim 1, wherein the polymer of the component (A) has a weight-average molecular weight of 1,400,000 to 2,400,000, and the polymer of the component (B) has a weight-average molecular weight of 100,000 to 200,000.

* * * * *